United States Patent [19]
Truesdale et al.

[11] Patent Number: 5,637,238
[45] Date of Patent: Jun. 10, 1997

[54] APPARATUS FOR ELECTRICAL DESTRUCTION OF MEDICAL INSTRUMENTS

[75] Inventors: Richard S. Truesdale, Fort Myers, Fla.; Ronald L. Nowak, Chagrin Falls; Ronald J. Garcowski, Parma, both of Ohio

[73] Assignee: Innovative Medical Equipment, Inc., Clearwater, Fla.

[21] Appl. No.: 381,638

[22] Filed: Jan. 31, 1995

[51] Int. Cl.$^6$ .......................... B23K 11/22; A61G 12/00; A61L 11/00
[52] U.S. Cl. .......................................................... 219/68
[58] Field of Search ................................................ 219/68

[56] References Cited

U.S. PATENT DOCUMENTS

| | | |
|---|---|---|
| 1,502,932 | 7/1924 | Young . |
| 2,101,700 | 12/1937 | Chestnut, Jr. . |
| 2,606,266 | 8/1952 | Duch et al. . |
| 3,091,145 | 5/1963 | Manganelli . |
| 3,469,750 | 9/1969 | Vanderbeck . |
| 3,683,733 | 8/1972 | Johan et al. . |
| 3,750,966 | 8/1973 | Anderson . |
| 3,851,555 | 12/1974 | Eldridge et al. . |
| 3,929,295 | 12/1975 | Montalbano . |
| 3,958,765 | 5/1976 | Musselman . |
| 4,040,425 | 8/1977 | Goodling et al. . |
| 4,205,794 | 6/1980 | Horton et al. . |
| 4,255,996 | 3/1981 | Choksi et al. . |
| 4,275,628 | 6/1981 | Greenhouse . |
| 4,315,448 | 2/1982 | Ball . |
| 4,404,881 | 9/1983 | Hanifl . |
| 4,447,694 | 5/1984 | Brochier et al. . |
| 4,531,437 | 7/1985 | Szablak et al. ......................... 83/165 |
| 4,628,169 | 12/1986 | Ch'ing-Lung ........................... 219/68 |
| 4,877,934 | 10/1989 | Spinello ................................. 219/68 |
| 4,905,916 | 3/1990 | Sorwick . |
| 4,961,541 | 10/1990 | Hashimoto . |
| 4,965,426 | 10/1990 | Colombo ................................ 219/68 |
| 5,046,669 | 9/1991 | Wallace et al. . |
| 5,076,178 | 12/1991 | Kohl et al. ............................. 110/250 |
| 5,138,124 | 8/1992 | Kirk et al. .............................. 219/68 |
| 5,212,362 | 5/1993 | Burden et al. .......................... 219/68 |
| 5,268,549 | 12/1993 | Butler .................................... 219/68 |
| 5,300,752 | 4/1994 | Elmerick et al. ....................... 219/68 |
| 5,329,087 | 7/1994 | Kohl et al. ............................. 219/68 |
| 5,391,849 | 2/1995 | Furuya et al. .......................... 219/68 |

*Primary Examiner*—Geoffrey S. Evans
*Attorney, Agent, or Firm*—Renner, Kenner, Greive, Bobak, Taylor & Weber

[57] ABSTRACT

A hypodermic needle destruction system utilizes a primary sub-housing with a cartridge demountably secured to the primary sub-housing. First and second electrodes are disposed within the cartridge. A guide is incorporated in one of the electrodes for accepting a metallic medical instrument for destruction. The guide directs the metallic medical instrument such that insertion thereof in the guide effects an electrical connection between the first and second electrodes. Atleast one of the electrodes is linearly reciprocated with respect to the other, and a sufficient level of electrical energy is applied across the first and second electrodes to cause the electrical destruction of the medical instrument positioned in electrical contact across the first and second electrodes. The present arrangement utilizes two, inter-related electrical power systems which provide two discrete energy levels, whether AC or DC. In either event, both the low and the high electrical energy systems are activated by needle insertion. The high energy system is operable to supply the power necessary to destroy the needle, to operate a fan and to cause at least one of the electrodes to move between fixed limits. A predetermined, subsequent period of time after the medical instrument is fully destroyed, the circuitry will turn off both the high and the low energy electrical systems.

14 Claims, 12 Drawing Sheets

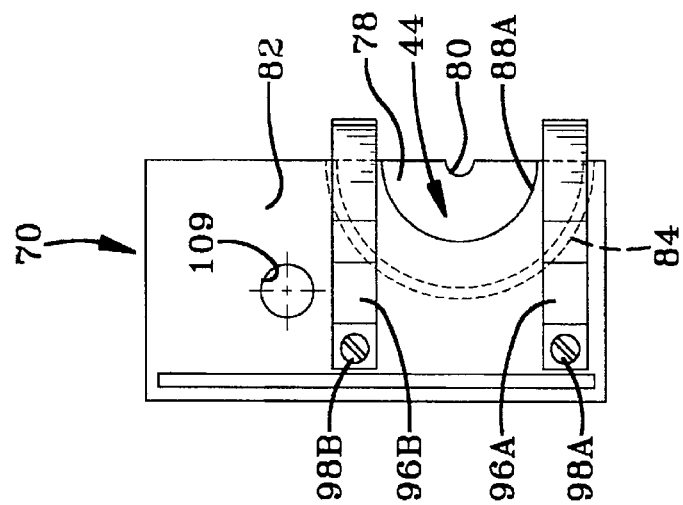
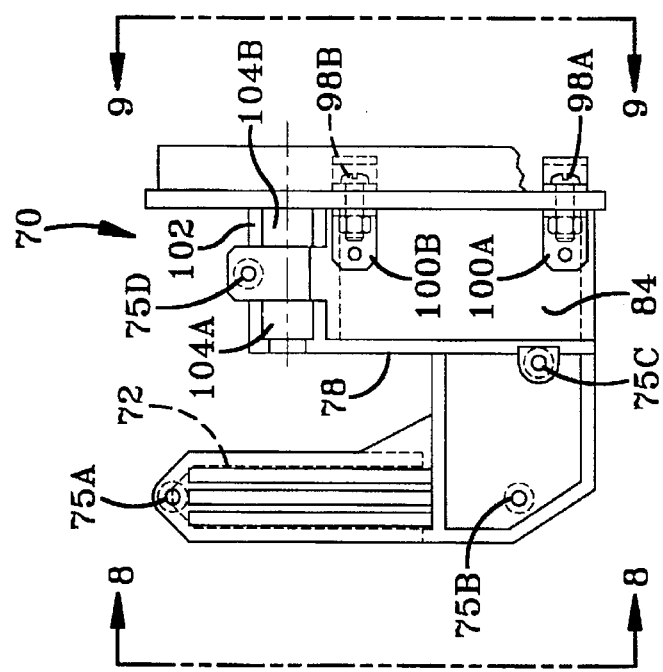
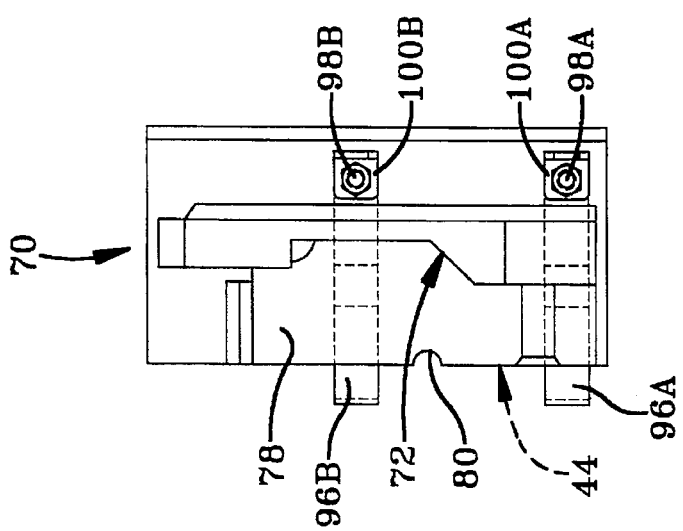
FIG-9
FIG-7
FIG-8

5,637,238

APPARATUS FOR ELECTRICAL DESTRUCTION OF MEDICAL INSTRUMENTS

TECHNICAL FIELD

The present invention relates generally to an apparatus for the destruction of metallic medical instruments by using electrical energy. More particularly, the present invention relates to an apparatus that electrically reduces the metallic, medical instrument to swarf. Specifically, the present invention relates to the destruction of medical instruments such as hypodermic needles by passing electrical energy through the instruments for which disposal is desired as the instrument spans two electrodes at least one of which oscillates, or reciprocates, with respect to the other.

BACKGROUND OF THE INVENTION

One of the more important activities for medical safety is the disposal of used medical instruments, and particularly disposable, metallic, hypodermic needles. Disposable hypodermic needles are widely used in hospitals and other medical facilities to draw body fluids from, and to inject medications into, patients. These needles are made disposable because of the difficulties, and inefficiencies, involved in sterilizing and sharpening hypodermic needles for reuse. Inasmuch as the needles are intended to be discarded after use, a problem arises as to their safe post-use storage and disposal.

In virtually every state it is illegal to discard used hypodermic needles as ordinary waste inasmuch as their sharp points, as well as the disease organisms carried on such needles, may injure hospital and/or waste disposal personnel. Moreover, there is also the very important need to prevent the disposed needles from being used by others, either recklessly or for illegal purposes. Because the current state of the art relating to the destruction of hypodermic needles is so unsatisfactory, untold quantities of such medical instruments are not being destroyed after use but are being illegally foisted on the environment, with disastrous results.

Many systems and apparatus, both mechanical and electrical, have been proposed over the years, but the prior proposals have each been deemed to be unsatisfactory.

For example, the prior known mechanical systems for hypodermic needle destruction have simply either crushed or broken the needles. Although these devices do prevent the reuse of the needles, such devices often serve to multiply the number of sharp points available inadvertently to pierce unwary humans. In addition, such disposal does not, in any way, neutralize any body fluids inadvertently retained on, or in, the needles. One example of such an arrangement is disclosed in U.S. Pat. No. 4,531,437 issued on Jul. 30, 1985.

In order to attempt to neutralize the body fluids retained in, or on, the needles, as well as any disease organisms present in those fluids, incineration of the disposable needles has also been utilized. Bulk incineration of accumulated needles, however, poses the continued threat of injury during that period of time beginning immediately following their usage and extending until the needles are actually received in the incinerator. Moreover, if the incinerating temperature is not sufficient to destroy the needle it continues to be a hazard, an unfortunate situation that has occurred in the past.

The period of potential exposure to needles that are contaminated has been reduced by supplying portable devices that are available to incinerate the needles electrically immediately after they have been used. The prior known electrical systems generally use electrical resistance heating to incinerate the needle. These systems have used both stationary electrodes, or relatively movable electrodes. One form of the movable electrode systems encompass arrangements wherein the needle is moved relative to the electrode, such as disclosed in U.S. Pat. No. 4,877,934, issued Oct. 31, 1989. In other forms of the movable electrode systems one of the electrodes is rotated relative to the needle, such as disclosed in U.S. Pat. No. 5,138,124, issued on Aug. 11, 1992. Heretofore, movable electrode systems, without further processing of the needle, leave at least one portion of the needle with a sharp end, even after the needle has been significantly destroyed.

The stationary electrode systems, such as that shown in U.S. Pat. No. 4,965,426 issued Oct. 23, 1990, are similar to the movable electrode systems currently in use. However, these systems generally do not destroy as much of the overall length of the needle as the movable systems do. These systems rely on the melting process to leave a rounded end, and thus do not assure the operator that the end is indeed blunt.

Even in the most advanced of the prior known systems the swarf must eventually be emptied, and most workers are fearful of having to open the apparatus to empty the residue. Even though they know that the swarf does not contain sharp points, they are fearful of inhaling any dust that might become airborne during the emptying process.

Careful attention has also disclosed that users of the electrical disposal devices are fearful of any gaseous vapor, or electrical sparks, escaping back into the atmosphere during operation of such devices.

It is thus apparent that a need remains for an improved method and apparatus for destroying metallic, medical instruments, and particularly hypodermic needles, in a more effective and efficient manner. The present invention is directed to that objective.

SUMMARY OF THE INVENTION

It is, therefore, a primary object of the present invention to provide a novel disposal system for metallic, medical instruments, such as hypodermic needles, wherein any remaining stub is blunted.

It is another object of the present invention to provide a novel disposal system for metallic, medical instruments, as above, wherein any body fluids inadvertently retained on, or in, the needles—as well as any disease organism carried by those fluids—is neutralized.

It is a further object of the present invention to provide a novel disposal system for metallic, medical instruments, as above, wherein the instrument to be destroyed spans two electrodes at least one of which oscillates, or reciprocates, with respect to the other.

It is yet another object of the present invention to provide a novel disposal system for metallic, medical instruments, as above, wherein the swarf resulting from the destruction of the medical instruments and any body fluid which is injected into the apparatus prior to neutralization are retained in a cartridge that can itself be destroyed without opening.

It is yet a further object of the present invention to provide a novel disposal system for metallic, medical instruments, as above, wherein gaseous vapor, or electrical sparks, are precluded from escaping back into the atmosphere during operation of the device.

It is a still further object of the present invention to provide a novel disposal system for metallic, medical instruments, as above, wherein the control functions may be accomplished with a low energy, electrical circuit and destruction of the needle may be accomplished with a high energy, electrical circuit.

It is an even further object of the present invention to provide a novel disposal system for metallic, medical instruments, as above, wherein the pair of spaced, relatively reciprocating electrodes are utilized to respond to the placement of a metallic, medical instrument thereacross to activate both electrical circuits.

These and other objects of the invention, as well as the advantages thereof over existing and prior art forms, which will be apparent in view of the following detailed specification, are accomplished by means hereinafter described and claimed.

In general, a disposal system embodying the concepts of the present invention utilizes a primary sub-housing with a cartridge demountably secured to the primary sub-housing. First and second electrodes are disposed within the cartridge. A guide means is incorporated in one of the electrodes for accepting a metallic, medical instrument for destruction. The guide means directs the metallic, medical instrument such that insertion thereof in the guide means effects an electrical connection between the first and second electrodes. At least one of the electrodes oscillates with respect to the other, and a sufficient level of electrical energy is applied across the first and second electrodes to cause the electrical destruction of the metallic, medical instrument positioned in electrical contact across the first and second electrodes.

While systems utilizing a single electrical system are convenient, it is much more economical and efficient to use two, inter-related electrical power systems which provide two discrete electrical energy levels, and the present invention provides such a system.

Both the low and the high energy electrical systems are activated by needle insertion. The high energy electrical system is operable to supply the power necessary to: destroy the metallic, medical instrument; to operate a fan; and, to cause at least one of the electrodes to move within a reciprocating path. After the metallic, medical instrument is fully destroyed, the electrodes will, after a predetermined period of time, turn off both the high and the low electrical energy systems.

To acquaint persons skilled in the arts most closely related to the present invention, one preferred embodiment of an electrical disposal system for medical instruments that illustrates a best mode now contemplated for putting the invention into practice is described herein by, and with reference to, the annexed drawings that form a part of the specification. The exemplary disposal system is described in detail without attempting to show all of the various forms and modification in which the invention might be embodied. As such, the embodiment shown and described herein is illustrative, and as will become apparent to those skilled in these arts can be modified in numerous ways within the spirit and scope of the invention; the invention being measured by the appended claims and not by the details of the specification.

BRIEF DESCRIPTION OF THE DRAWINGS

FIG. 7 is a top plan view of the mounting block utilized interiorly of the primary sub-housing;

FIG. 8 is a rear elevation of the mounting block taken substantially along line 8—8 of FIG. 7;

FIG. 9 is a frontal elevation of the mounting block taken substantially along line 9—9 of FIG. 7;

DESCRIPTION OF AN EXEMPLARY EMBODIMENT

One representative form of an apparatus adapted for the electrical destruction of medical instruments, and embodying the concepts of the present invention, is designated generally by the numeral 10 on the accompanying drawings. The representative apparatus 10 is particularly adapted for the destruction of hypodermic needles, but as will become apparent, the apparatus 10 may be adapted for the destruction of a wide variety of metallic, medical instruments. Even so, the following description will, for the convenience of the reader, be specifically directed to hypodermic needles, although it is to be understood that the concepts of the present invention are readily adaptable to a wide variety of metallic, medical instruments.

Figure 1:
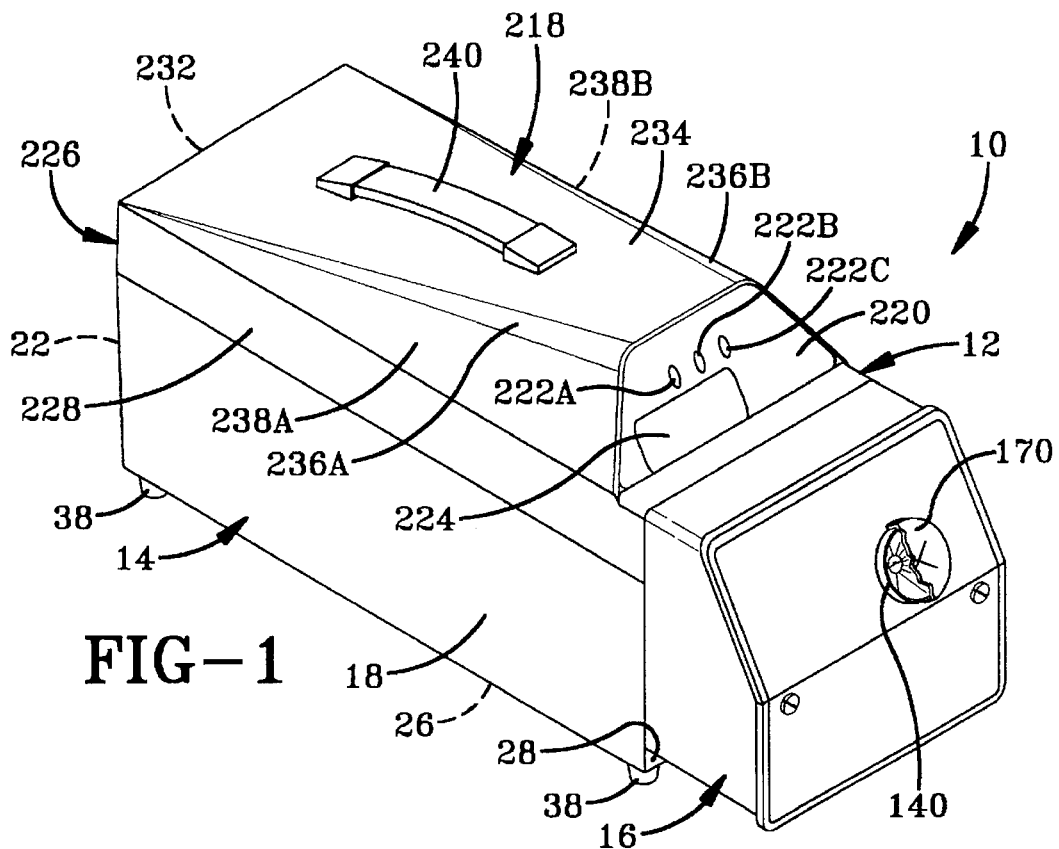
FIG. 1 is a frontal perspective of an apparatus incorporating the concepts of the present invention.
Figure 2:
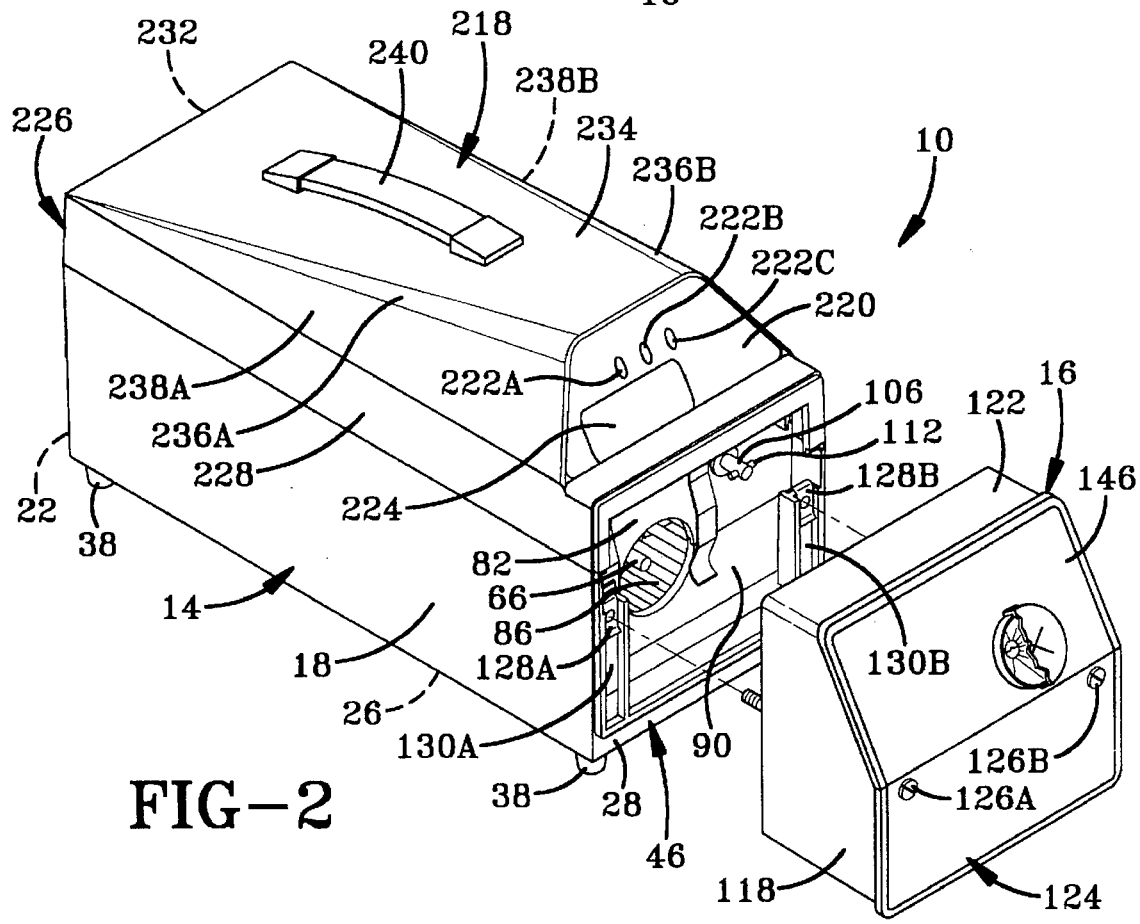
FIG. 2 is a view similar to FIG. 1, but exploded to depict the separability of the cartridge sub-housing from the primary sub-housing.

As seen in FIGS. 1 and 2, the overall housing 12 for the apparatus is divided into a primary sub-housing 14, and an associated sub-housing in the nature of a disposable, swarf-collecting, fluid-retaining cartridge that is demountably secured to the primary sub-housing 14. The cartridge sub-housing is designated by the numeral 16.

Figure 3:
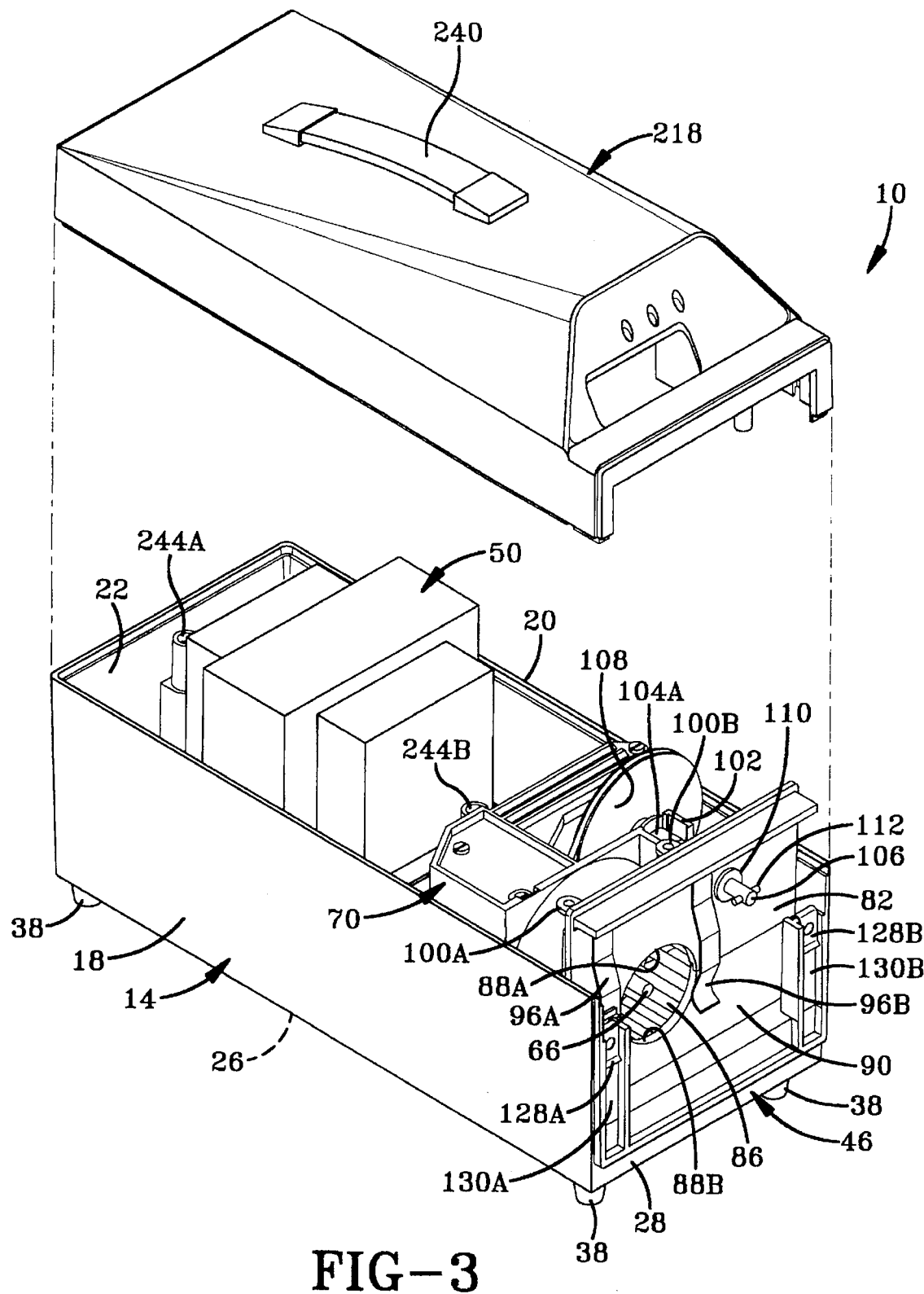
FIG. 3 is also a view similar to FIG. 1, but without depicting the cartridge sub-housing, and exploded to reveal the inter-relation of the cover with respect to the primary sub-housing.
Figure 4:
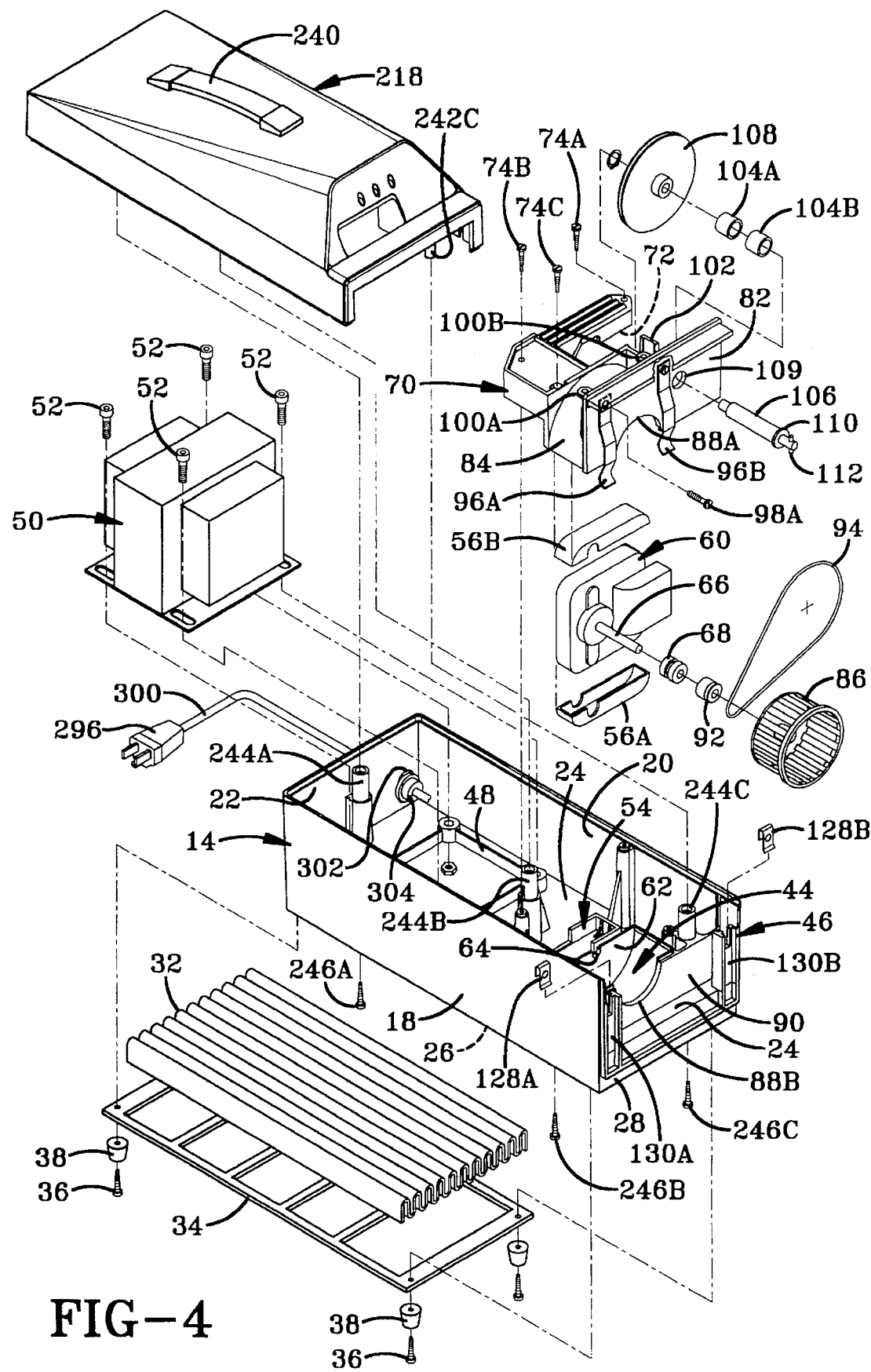
FIG. 4 is an exploded perspective of the primary sub-housing and the components operably received therein.

As best seen in FIGS. 3 through 6, the primary sub-housing 14 has laterally spaced side walls 18 and 20, an end, or rear, wall 22 and a base 24 that is offset upwardly from the lower edge 26 of the primary sub-housing 14—the lower edge 26 being collectively defined by the lower edges of the peripheral walls 18, 20 and 22 as well as the lip 28 that extends downwardly at the front of the primary sub-housing 12. The upwardly offset location of the base 24 defines a recess 30 on the underside of the primary sub-housing 14 that is adapted to receive an environment-protecting filter 32 which may be secured within the recess 30 by a retaining grille 34. As best seen in FIG. 4, the retaining grille 34 may be secured to the primary sub-housing 14 by a plurality of fastening means, such as the self-threading screws, 36. Non-skid feet 38 may also be appropriately secured to the primary sub-housing 14 by the screws 36.

Figure 5:
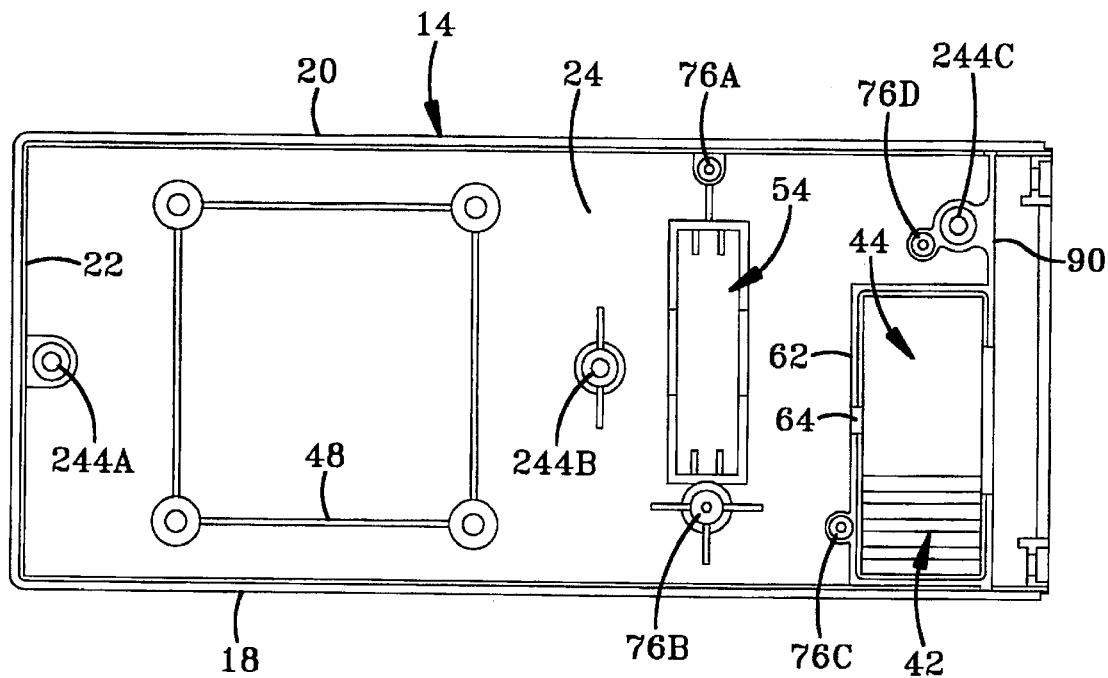
FIG. 5 is an enlarged top plan of the primary sub-housing, with all the internal components removed.
Figure 6:
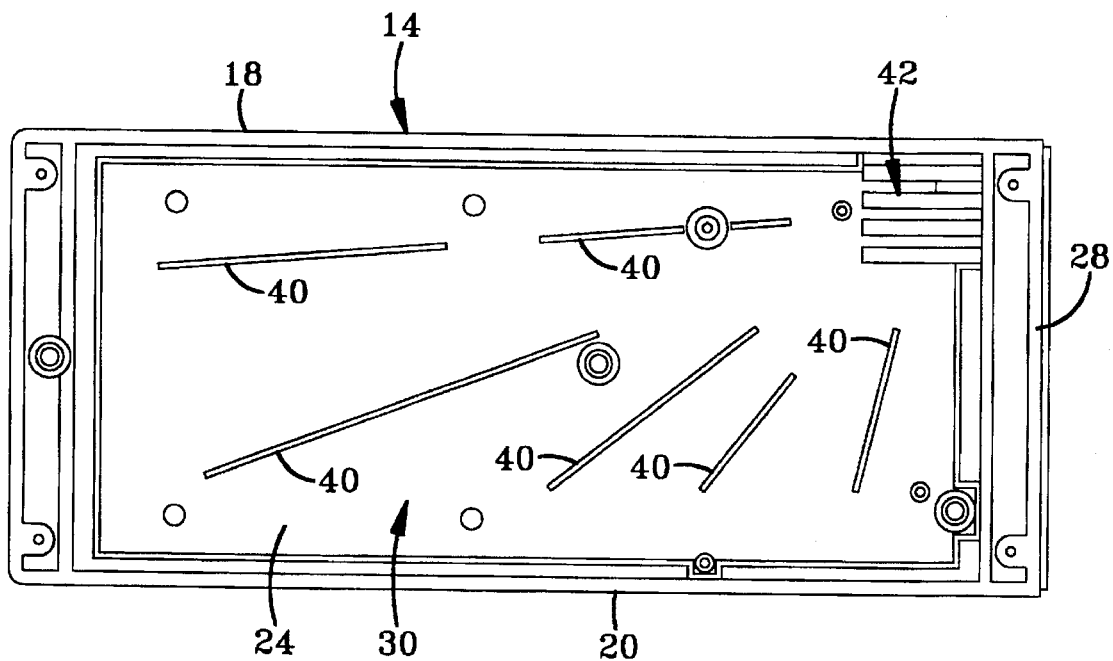
FIG. 6 is a bottom plan view of the primary sub-housing with the internal components removed, and drawn to the same scale as FIG. 5.

The base 24 may, as shown in FIG. 6, be provided with a plurality of spacing ribs 40 that extend in a generally radial fashion outwardly from a grilled aperture 42 through which a fan-receiving chamber 44 (FIGS. 4 and 5) communicates with the recess 30. As such, the spacing ribs 40 permit the free flow of air within that portion of the recess 30 between the base 24 and the filter 32. This permits free access of the air entering the recess 30 through the grilled aperture 42 to the full surface of the filter 32. The environmental protecting filter 32 serves primarily to preclude the emission of aerosols, whether toxic or not, from the interior of the apparatus 10. Depending, therefore, on the use to which the particular needles to be disposed had been put, it might be sufficient to employ a high efficiency aerosol particulate filter 32 capable of a 99.97% dioctylphalate (DOP) efficiency for removing particulate as small as 0.3 microns (commercially available as a HEPA filter). On the other hand, for some installations it may be necessary to employ a aerosol particulate filter 32 capable of a 99.998% DOP efficiency for removing particulate matter as small as 0.1 microns (commercially available as an ULPA filter).

With continued reference to FIGS. 4 and 5, that surface of the base 24 which faces the interior of the primary sub-housing 14 may present a rectangular mounting pedestal 48 (also best seen in FIGS. 4 and 5) on which a multi-tap transformer 50 may be secured, as by four nut and bolt combinations 52. Forwardly of the mounting pedestal 48 the base 24 presents a raised edge, motor-mounting recess 54 that may receive a first vibration damper 56A (FIG. 4). The first vibration damper 56A is formed to encase that portion of a motor 60 which is received within the recess 54. A chamber wall 62 is disposed forwardly of the motor-mounting recess 54 to define the rearmost boundary of the fan-receiving chamber 44, and the chamber wall 62 may have a notch 64 that rotatably receives the motor shaft 66. A bearing member 68 is preferably received within the notch 64 to provide not only a low friction support for the shaft 66 but also to seal the fan-receiving chamber 44 from the remainder of the primary sub-housing 14.

As previewed in the previous paragraph, and as will appear in the detailed description which follows, a particular structural member, component or arrangement may be employed at more than one location. When referring generally to that type of structural member, component or arrangement a common numerical designation shall be employed. However, when one of the structural members, components or arrangements so identified is to be individually identified it shall be referenced by virtue of a letter suffix employed in combination with the numerical designation employed for general identification of that structural member, component or arrangement. Thus, there are at least two vibrations dampers which are generally identified by the numeral 56, but the specific, individual vibration dampers are, therefore, identified as 56A and 56B in the specification and on the drawings. This same suffix convention shall be employed throughout the specification.

A generally U-shaped, mounting block 70 (FIGS. 4 and 7 through 9) may be selectively secured within the primary sub-housing 14, and the mounting block 70 presents a motor-mounting recess 72 that is disposed in opposition to the motor-mounting recess 54 presented from the base 24 of the primary sub-housing 14. A second vibration damper 56B may be received in the recess 72 such that when the mounting block 70 is secured to the sub-housing 14—as by the four self-threading screws 74 which extend through bores 75A through 75D to engage the opposed stand-offs 76A through 76D, respectively (as shown in FIG. 5)—the vibration dampers 56A and 56B will capture the motor 60 therebetween. The mounting block 70 also includes a chamber wall 78 that is opposed to the chamber wall 62 and defines one side of the fan-receiving chamber 44 when the mounting block 70 is operably secured within the primary sub-housing 12. The chamber wall 78 may also have a notch 80 that rotatably receives the motor shaft 66. The bearing member 68 would, therefore, be received within the cylindrical aperture formed by the opposed notches 64 and 80 to provide a support for the shaft 66 and also to complete the seal between the fan-receiving chamber 44 and the remainder of the primary sub-housing 14.

The mounting block 70 also has a second wall 82 that is longitudinally spaced forwardly from the first wall 78, and an arcuate chamber wall 84 extends longitudinally therebetween to complete the definition of the fan-receiving chamber 44. An annular fan member 86 is received within the chamber 44 to be operatively connected to, and driven by, the shaft 66 of the motor 60. The second wall 82 has a semi-cylindrical aperture 88A that is opposed to a semi-cylindrical aperture 88B in an opposed transverse wall 90 that extends upwardly from the base 24 and laterally between the side walls 18 and 20 of the primary sub-housing 14. The opposed semi-cylindrical apertures 88A and 88B will, as will hereinafter become more apparent, constitute the intake to the fan-receiving chamber 44.

A drive pulley 92 (FIG. 4) is secured to that portion of the shaft 66 which extends between the motor 60 and the opposed walls 62 and 78. A drive belt 94 engages the pulley 92 for a purpose more fully hereinafter described.

A pair of resilient, electrical contact bars 96A and 96B are mounted in laterally spaced relation to overlie a portion of the second wall 82. By judicious selection of the lateral spacing, the contact bars 96A and 96B will be respectively positioned, with one on each side of the intake to the chamber 44 formed by the semi-cylindrical apertures 88A and 88B. The separate nut and bolt combinations 98A and 98B, respectively, by which the contact bars 96A and 96B are secured to the mounting block 70 may also each receive an electrical spade connector 100 by which to effect an electrical connection between the transformer and the nut and bolt combinations 98. That is, a spade connector 100A may be secured by nut and bolt combination 98A, and a spade connector 100B may be secured by nut and bolt combination 98B.

A bearing support 102 extends rearwardly from the wall 82 to receive the sleeve bearings 104 that stabilizes an electrode drive shaft 106. As shown, two axially spaced bearings 104A and 104B may be employed. A driven pulley 108 may be secured to the longitudinally rearward end portion of the electrode drive shaft 106. The driven pulley 108 is aligned with the drive pulley 92 to receive the drive belt 94. To slow the rotation of the electrode drive shaft 106 relative to the rotation of the motor shaft 66, it may be desirable to provide a diametral differential between the drive and driven pulleys 92 and 108, respectively, on the order of about 5-to-1.

The longitudinally forward end portion of the electrode drive shaft 106 extends through an aperture 109 in the wall 82 to present a stop which may comprise a shoulder formed directly on the shaft 106 or which may be effected by a washer 110, as depicted. An engaging dog 112 extends radially outwardly from one or both sides of the electrode drive shaft 106 for a purpose more fully hereinafter described.

As best seen in FIGS. 10 through 14, the swarf-collecting, fluid-retaining cartridge, or sub-housing, 16 is demountably secured to the open front 46 of the primary sub-housing 14, and upwardly of the lip 28, by means also hereinafter more fully described. The cartridge 16 itself has a base wall 114, a rear wall 116, laterally spaced side walls 118 and 120, a top wall 122 and a front wall 124 that is only removable when the cartridge 16 is not mounted on the primary sub-housing 14.

The cartridge 16 is demountably attachable to the primary sub-housing 14 as by the connecting means in the nature of machine-type screws 126A and 126B that extend through the cartridge 16 to be received in what are commonly referred to as Tinnerman nuts 128A and 128B that are supported from boxed flanges 130A and 130B located adjacent the respective side walls 18 and 20 of the primary sub-housing 14, as best seen in FIGS. 2 through 4. Preferably, the head 127 of each screw 126 should be designed to receive a unique tool so that only authorized personnel may remove the cartridge from the primary sub-housing 14.

To ensure that the pathway for the connecting means 126 will not provide any undesired access to, or from, the interior of the cartridge 16, closed first races 132A and 132B extend along the interior face of the respective side walls 118 and 120 of the cartridge 16. Second races 134A through 134D also extend along the respective side walls 118 and 120. The second races 134 receive the fastening means, such as by a plurality of self-threading screws 136, by which the front wall 124 is demountably attached to the remainder of the cartridge 16. Preferably, the head 137 of each screw 136 should also be designed to receive a unique tool so that only authorized personnel may remove the front wall 124 of the cartridge 16.

The cartridge 16 houses a fixedly positioned, non-movable, first electrode 140 and a uniquely movable, second electrode 142. The fixed electrode 140 is received within an opening 144 that penetrates the sloping portion 146 of the front wall 124. The fixedly positioned, first electrode 140 is mounted within the opening 144, as by a bowed snap ring 148 that is receivable within an annular recess 150 in the body portion 152 of the fixedly positioned, first electrode 140. As such, the snap ring 148 clamps the sloping portion 146 of the front wall 124 against a shoulder 154 on the body portion 152 of the fixed electrode 140.

Figure 15:
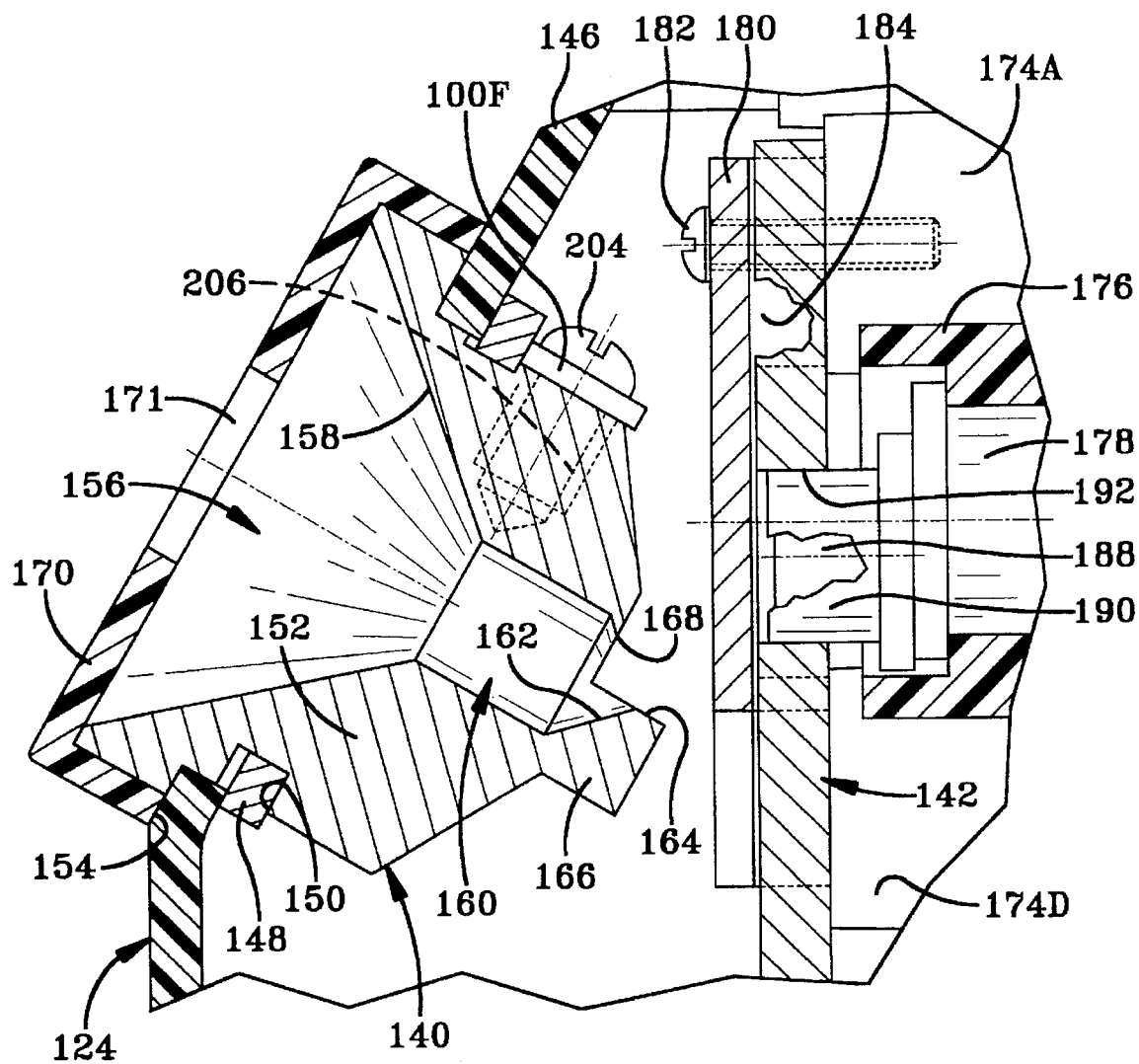
FIG. 15 is an enlarged portion of FIG. 14—the outline of the enlarged portion being delineated by the chain-line identified as "FIG-15" on FIG. 14.
Figure 16:
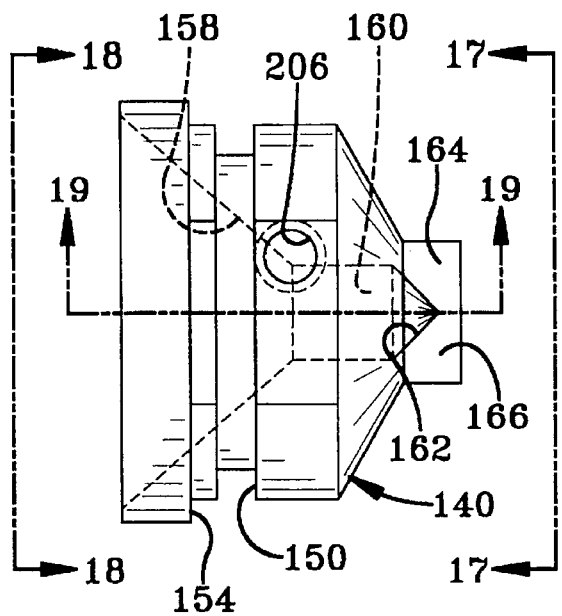
FIG. 16 is a side elevation of the fixed electrode that is depicted in cross-section in FIG. 15.
Figure 17:
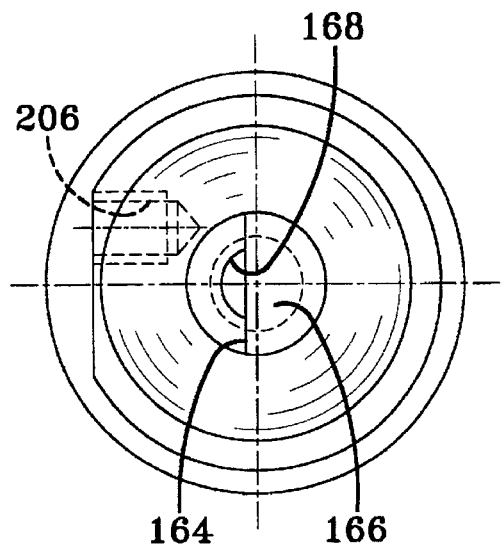
FIG. 17 is an end elevation taken substantially along line 17—17 of FIG. 16.
Figure 18:
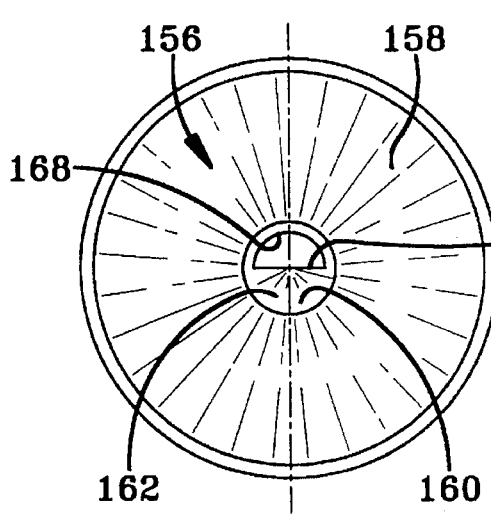
FIG. 18 is an end elevation taken substantially along line 18—18 of FIG. 64.

The fixedly positioned, first electrode 140 has a central opening 156 (FIG. 15) with an axially outermost, first, conical portion 158 that converges axially inwardly to merge into a cylindrical passage 160. The cylindrical passage 160 extends between the first, conically converging portion 158 and a second, conical portion 162 that converges to the chordal wall 164 of a deflecting terminus 166. The chordal wall 164 disposed in axially offset opposition to a semi-cylindrical rim 168 such that the generally opposed, but axially spaced, wall 164 and rim 168 impart stability to the medical instrument located therebetween as it engages the linearly reciprocating electrode 142. The diameter of the cylindrical passage 160 is chosen so that it will closely encase the needle insertably received therein in order to minimize the available space through which any sparks must travel to reach the exterior of the cartridge 16. On the other hand there must be a sufficient clearance between the needle and the cylindrical passage 160 in order to permit air to enter the cartridge in response to the action of the fan member 86.

A protective cap 170 that presents a flexible, slotted face 171 may be frictionally received over that portion of the fixed electrode 140 located on the outside of the front cover wall 124 to allow facile entry of a needle and environmental air drawn in by the fan member 86 but at the same time to preclude the escape of any sparks that are engendered by destruction of the needle against the linearly reciprocating electrode 142.

The second electrode 142 is mounted on the rear wall 116 of the cartridge 16 for movement between fixed limits. Specifically, the second electrode 142 may be in the form of a rectangular plate that is balanced across the edges of two, spaced, locating walls 172A and 172B. Locating wall 172A extends between stand-offs 174A and 174B, and locating wall 172B extends between stand-offs 174C and 174D. The stand-offs 174 may, as depicted, be located in a square matrix around an annular extension 176 within which a transfer shaft 178 is rotatably received. A guide plate 180 is mounted on the four stand offs 174 by a plurality of self-threading screws 182, and the guide plate 180 has a slideway 184 recessed into the rear face thereof to receive the second electrode 142.

The end of the rear portion of the transfer shaft 178 is bifurcated, as at 186, to engage the dog 112 on the electrode drive shaft 106. The frontal portion of the transfer shaft 178 terminates in an eccentrically located drive pin 188 that receives a dielectric bushing 190 that electrically insulates the transfer shaft 178 from the second electrode 142. The eccentric drive pin 188, on which the dielectric bushing 190 is mounted, is received within a laterally extending slot 192 in the second electrode 142. Thus, rotation of the transfer shaft 178 effects oscillating and reciprocating movement of the second electrode 142 between fixed limits. It should be understood that if the eccentricity of the drive pin 188 relative to the rotational axis of the transfer shaft 178 is minimized, the oscillation will appear to pulse, or vibrate. The rate of the periodic motion can, of course, be preselected by careful selection of the relative diameters of the drive pulley 92 and the driven pulley 108. In the preferred form of the invention the reciprocation is linear, and, in fact, constitutes a translational movement wherein all points on the moving electrode 142 will have, at any instant, the same velocity and direction of motion. Even though the preferred movement of the electrode 142 is translational linear reciprocation those skilled in the art can, therefore, select the specific oscillation, vibration or reciprocation desired for their purposes.

The rear wall 116 of the cartridge 16 is also provided with a grilled port 194 that aligns with the input to the fan-receiving chamber 44—the input being formed by the apertures 88A and 88B. The grilled port 194 is covered with a second filter 196. The second filter 196 is preferably a carbon filter which may be held in place by a removable grille 198 that may be mounted to the rear wall 116 of the cartridge 16 by two electrically conductive nut and bolt combination 200A and 200B. The purpose of the carbon filter 196 is to retain the swarf within the cartridge 16. As such, the filter 196 need only be capable of removing particles larger than about 100 microns.

Figure 10:
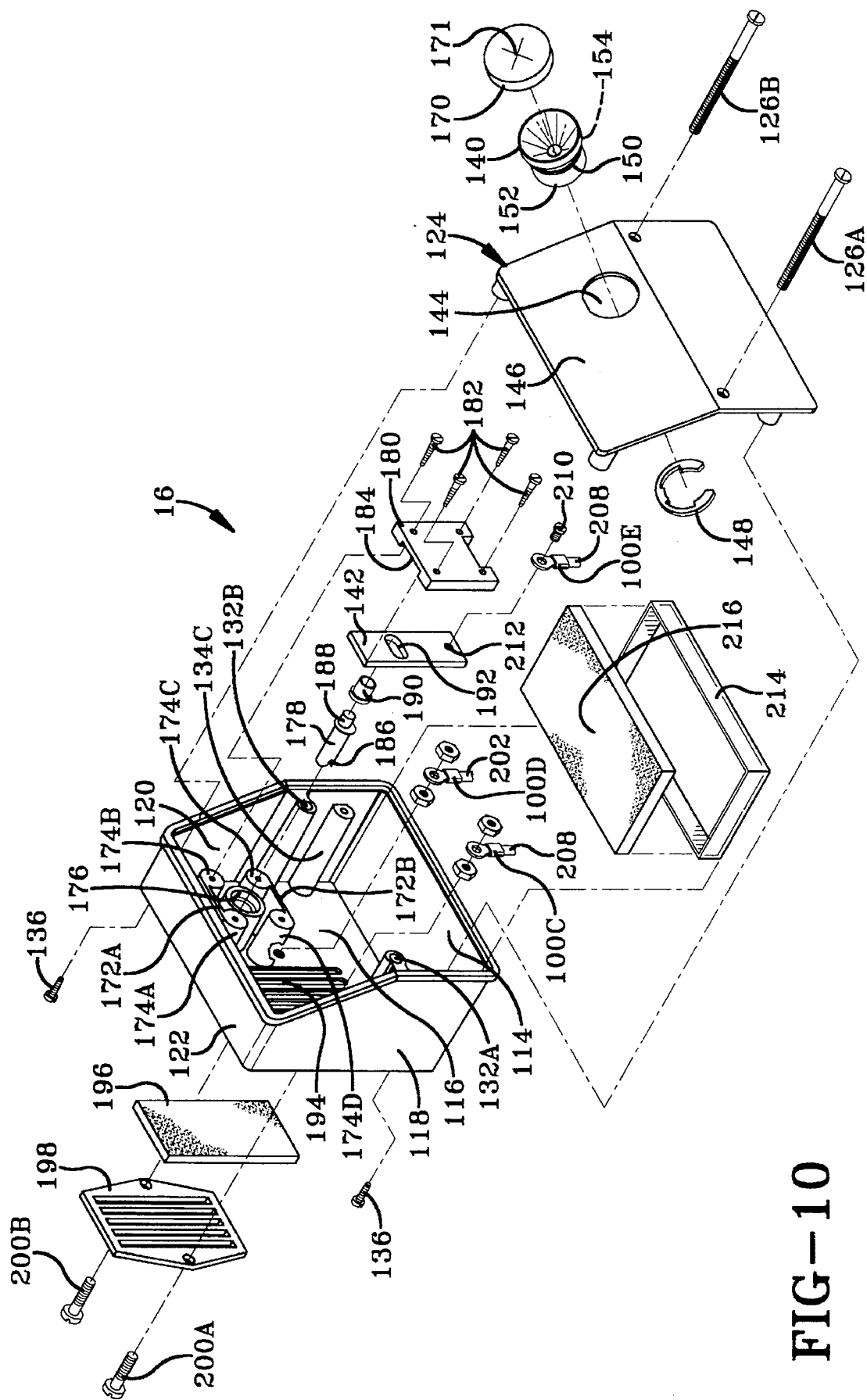
FIG. 10 is an exploded perspective of the cartridge sub-housing.
Figure 11:
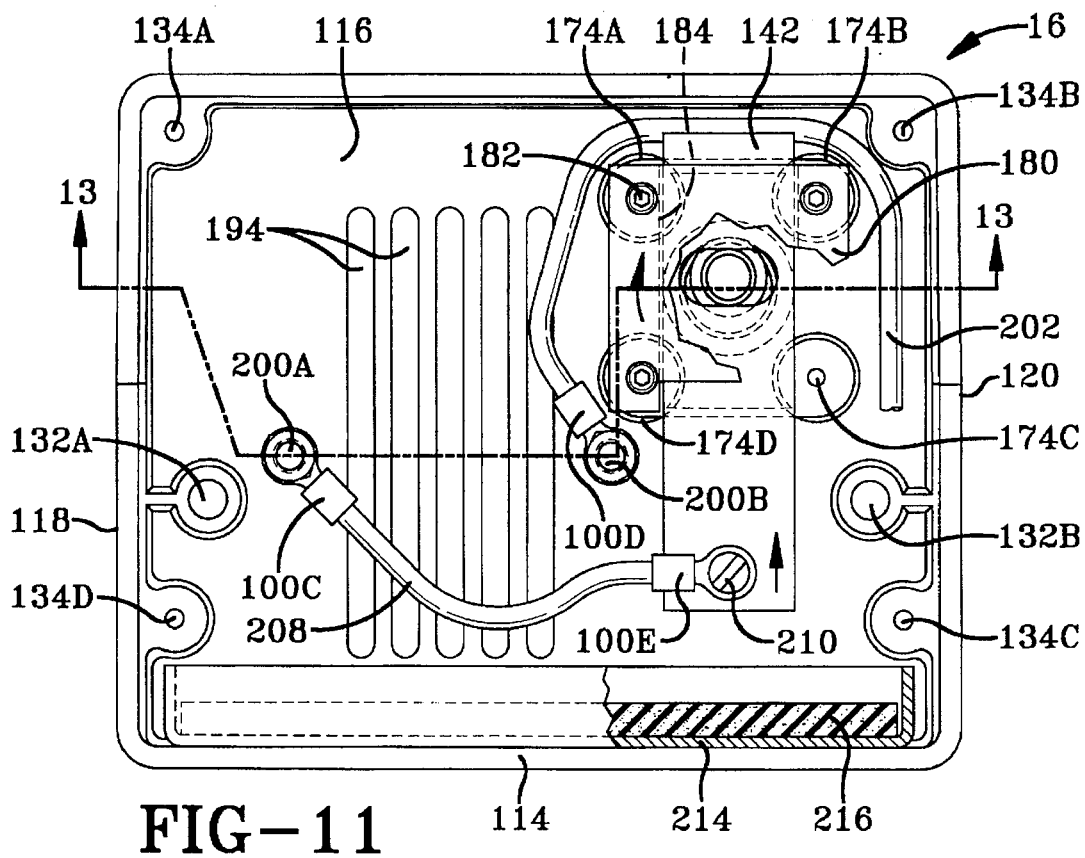
FIG. 11 is an enlarged frontal elevation of the cartridge sub-housing depicting the movable electrode at one end of its linear displacement, the view being partially broken away to reveal not only the mechanism by which the movable electrode is reciprocated but also the means by which to capture any residual liquids.
Figure 12:
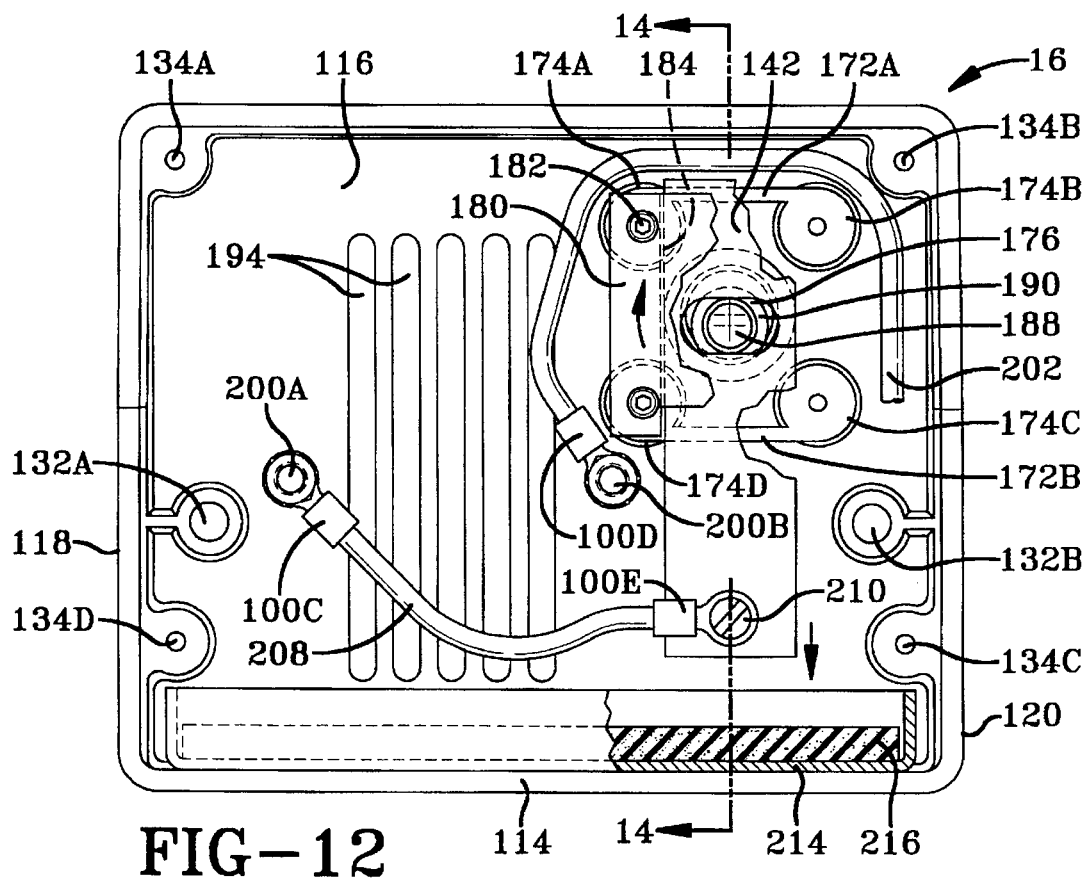
FIG. 12 is a view similar to FIG. 11, but depicting the movable electrode at the opposite end of its linear displacement.
Figure 13:
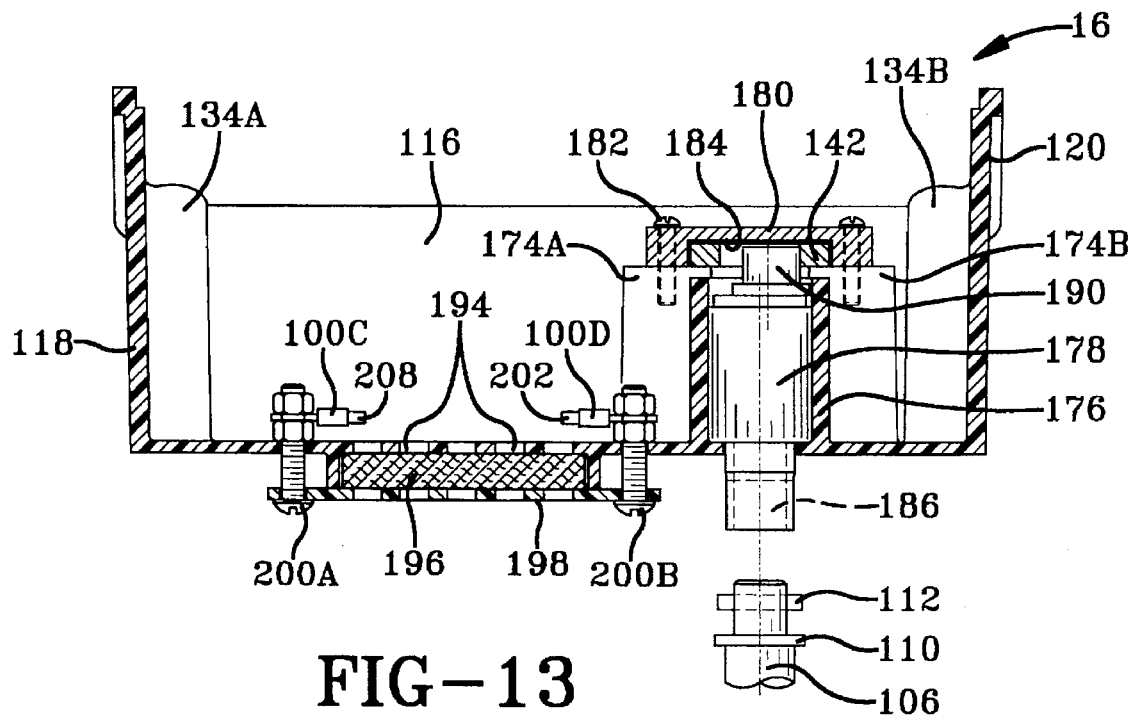
FIG. 13 is a transverse section taken substantially along line 13—13 of FIG. 11.
Figure 14:
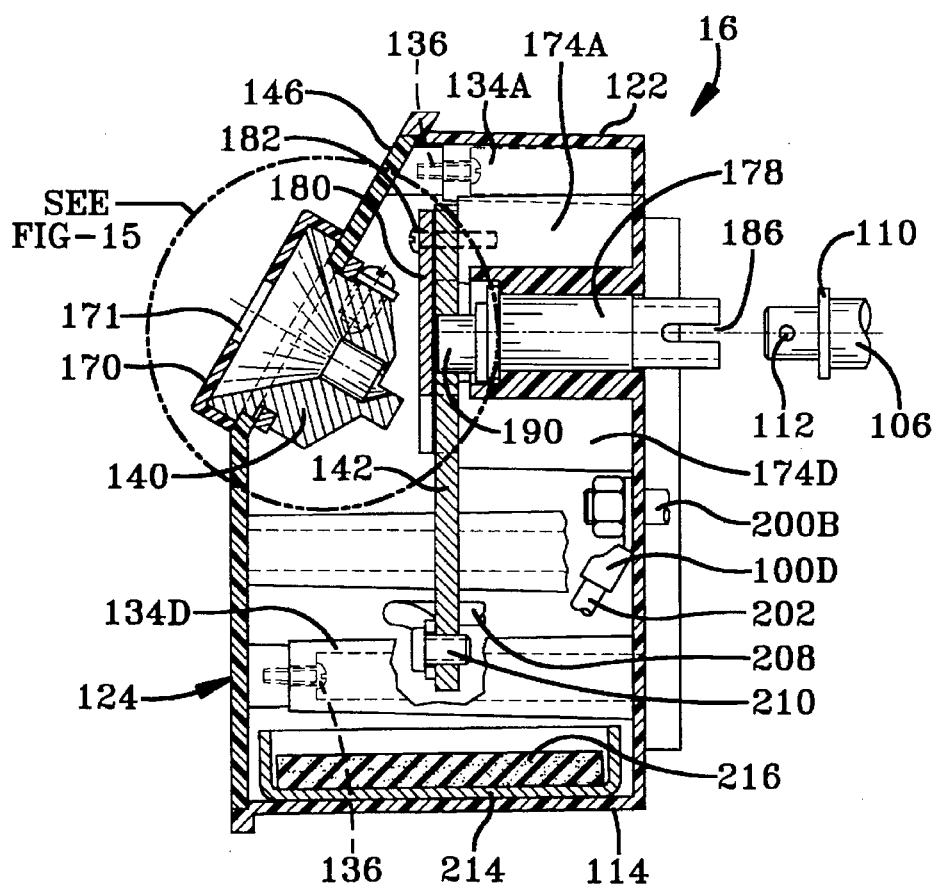
FIG. 14 is a vertical section taken substantially along line 14—14 of FIG. 12.

With continued reference to FIGS. 10 through 12, each nut and bolt combination 200 also mounts an electrical spade connector 100 within the cartridge 16. A wire 202 electrically joins the spade connector 100D with a spade connector 100F that is secured to electrode 140 by the cap screw 204 (FIG. 15) that is receivable within a threaded bore 206 in the body portion 152 of the fixed electrode 140. Similarly, a wire 208 electrically joins the spade connector 100C with a spade connector 100E that is secured to electrode 142 by the cap screw 210 that is receivable within a threaded bore 212 in electrode 142.

When the cartridge 16 is mounted on the primary sub-housing 14, the electrically conductive nut and bolt combinations 200A and 200B, respectively, engage the resilient contact bars 96A and 96B to effect a fast-make coupling and thereby complete the electrical circuit from the spade connectors 100A and 100B conjoined with the contact bars 96A and 96B to the two electrodes 140 and 142.

Also with reference to FIGS. 10 through 12 it can be observed that a metallic tray 214 may be received on the base wall 114 of the cartridge 16. The tray 214 is intended not only to receive the hot swarf as it drops from the movable electrode 142 but also to receive and contain any fluids that might not be vaporized by the heat produced as a result of the arcing of the electrical energy as it passes between the needle N and the electrodes 140 and 142. A heat-resistant sponge 216 may be secured within the tray 214 to absorb any fluids not vaporized and thereby assure their retention within the cartridge 16. A germicidal fluid may be absorbed into the sponge 216 prior to placing the apparatus 10 in service. Although not depicted, a germicidal lamp that is preferably a low wattage, low-pressure mercury arc variety having a radiation output primarily in the ultraviolet wavelengths may be located within the cartridge 16. The most desirable lamp would transmit ultraviolet energy of shorter wavelengths than the bulbs of most mercury lamps in order effectively to serve its germicidal purpose.

Figure 19:
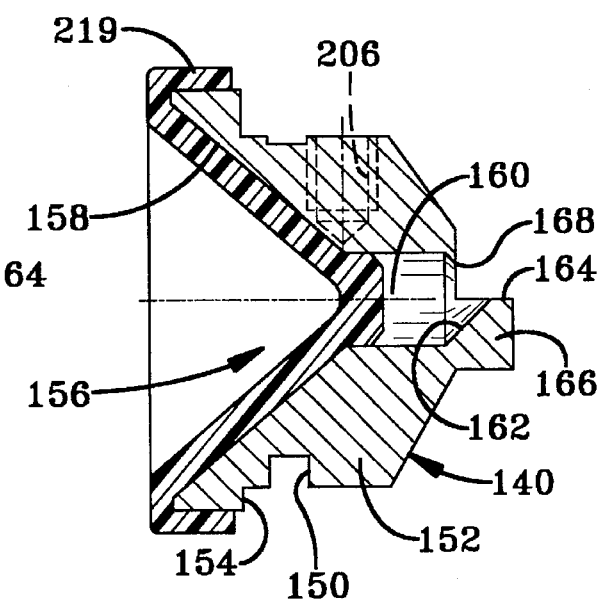
FIG. 19 is cross section taken substantially along line 19—19 of FIG. 16, but depicting a storage plug operatively inserted in the fixed electrode.

It should be appreciated that when the cartridge 16 is removed from the primary sub-housing 14 it is desirable to close the central opening 156 through the fixed electrode 140 of the full cartridge. As depicted in FIG. 19, a plug 219—which conforms to the conical wall 158, and perhaps the cylindrical passage 160 of the central opening 156—may be required to be substituted for the protective cap 170 effectively to seal the fixed electrode 140 after the cartridge 16 has been removed from the primary housing 12. Thus, when one cartridge 16 is filled and needs to be replaced with an empty cartridge 16, a plug 219 may be provided with the replacement cartridge 16. The protective cap 170 can easily be transferred from the full cartridge 16 to the empty cartridge 16, and the fixed electrode 140 on the full cartridge 16 may be closed with a plug 219.

Returning again to FIGS. 1 through 3, the primary sub-housing 14 has a cover 218. The cover 218 has a slanted, frontal surface 220 through which the control read-outs may be presented. For example, three round apertures may receive the light emitting diode (LED) displays 222A, 222B and 222C which, respectively, reflect: (1) that power is available to the apparatus 10; (2) that the apparatus 10 is in the process of effecting an electrical destruction of a needle; and, (3) that the cartridge is full and further usage of the apparatus 10 is precluded until the full cartridge 16 has been replaced with an empty cartridge. A rectilinear aperture may receive a four digit, read-out 224 that may tell, in selected units, the number of needles that have been destroyed by the apparatus 10, the remains of which are currently residing in the cartridge 16.

From the slanted, frontal surface 220, the cover 218 slopes downwardly and rearwardly to join the three-sided, rectilinear skirt 226 which opposingly mates with the side walls 18 and 20 as well as the rear wall 22 of the primary sub-housing 14. That is, the side walls 228 and 230, respectively, opposingly engage the side walls 18 and 20 of the primary sub-housing 14, and the rear wall 232 of the skirt 226 opposingly engages the rear wall 22 of the primary sub-housing 14. That portion of the cover 218 which slopes downwardly and rearwardly to join the skirt 226 comprises: the main upper panel 234—which joins the upper edge of the slanted, frontal surface 220 with the upper edge of the rear wall 232; two, smaller triangular panels 236A and 236B—which join the haunched edges of the slanted frontal surface 220 with the respective intersections of the rear wall 232 with the two side walls 228 and 230; and, the two larger triangular panels 238A and 238B—which conjoin the lateral edges of the slanted, frontal surface 220 with the respective side walls 228 and 230 of the skirt 226 as well as the two smaller triangular panels 230A and 230B. A handle 240 may, if desired, be provided on the main upper panel 234 of the cover 218.

Figure 20:
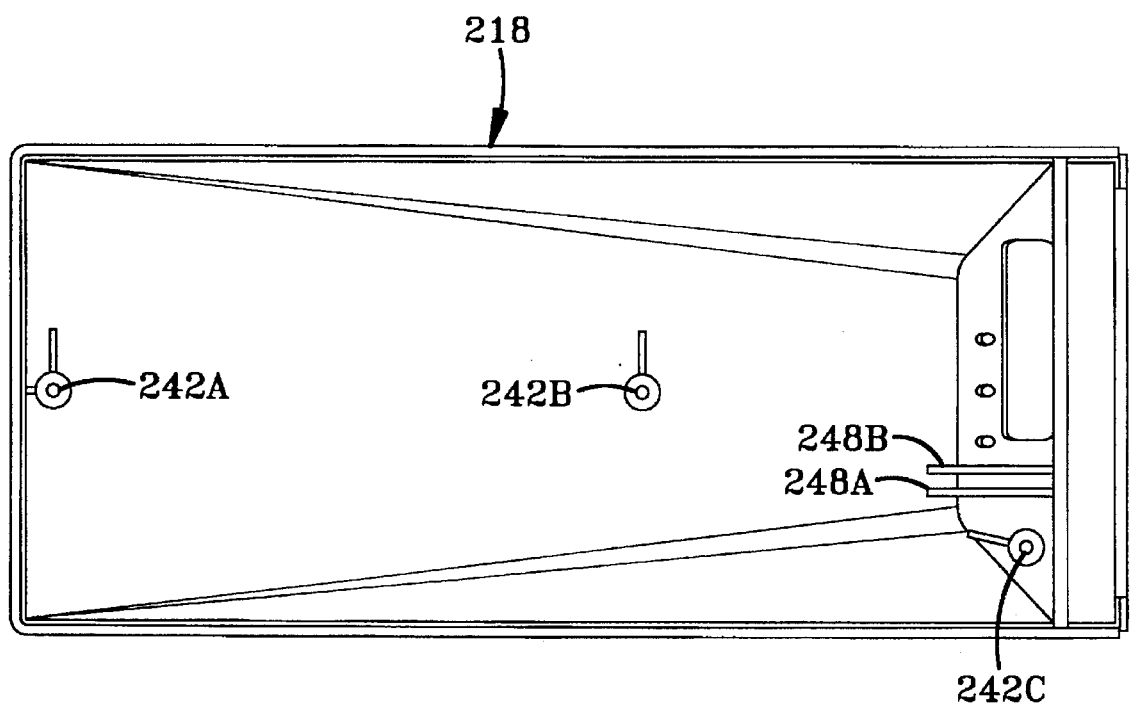
FIG. 20 is a bottom plan view of the cover employed with the primary sub-housing; and, FIG. 21 is a schematic wiring diagram for one mode of the circuitry that may be employed in the present invention.

A plurality of stand-offs 242A, 242B and 242C may be provided on the underside of the cover 218 (FIG. 20) opposingly to engage a like number of stand-offs 244 that extend upwardly from the base 24 of the primary sub-housing 14 (FIGS. 4 and 5). Self-threading screws 246 may extend upwardly within the stand-offs 244 threadably to engage the opposed stand-offs 242 and thereby secure the cover 218 to the primary sub-housing 14. Here, too, disassembly is discouraged by virtue of the fact that the screws 246 can not be accessed unless the environment-protecting filter 32 is first removed.

Interiorly of the cover 218 a pair of laterally spaced, longitudinally oriented blades 248A and 248B extend downwardly to engage, and thus serve to retain, the sleeve bearings 104 received within the bearing supports 102 presented from the mounting block 70.

The present invention, while typically utilizing relatively low DC energy for the control circuits and higher AC energy for the needle destruction as well as for the reciprocation of the movable electrode and the operation of the fan, a person who understands the concepts described herein would be readily capable of operating the apparatus solely with DC voltage, as in the situation where one desired to operate the apparatus 10 from a DC power source in a vehicle. Thus, the particular circuitry of choice will likely depend upon the nature of the environment in which the particular apparatus 10 is to be used.

Figure 21:
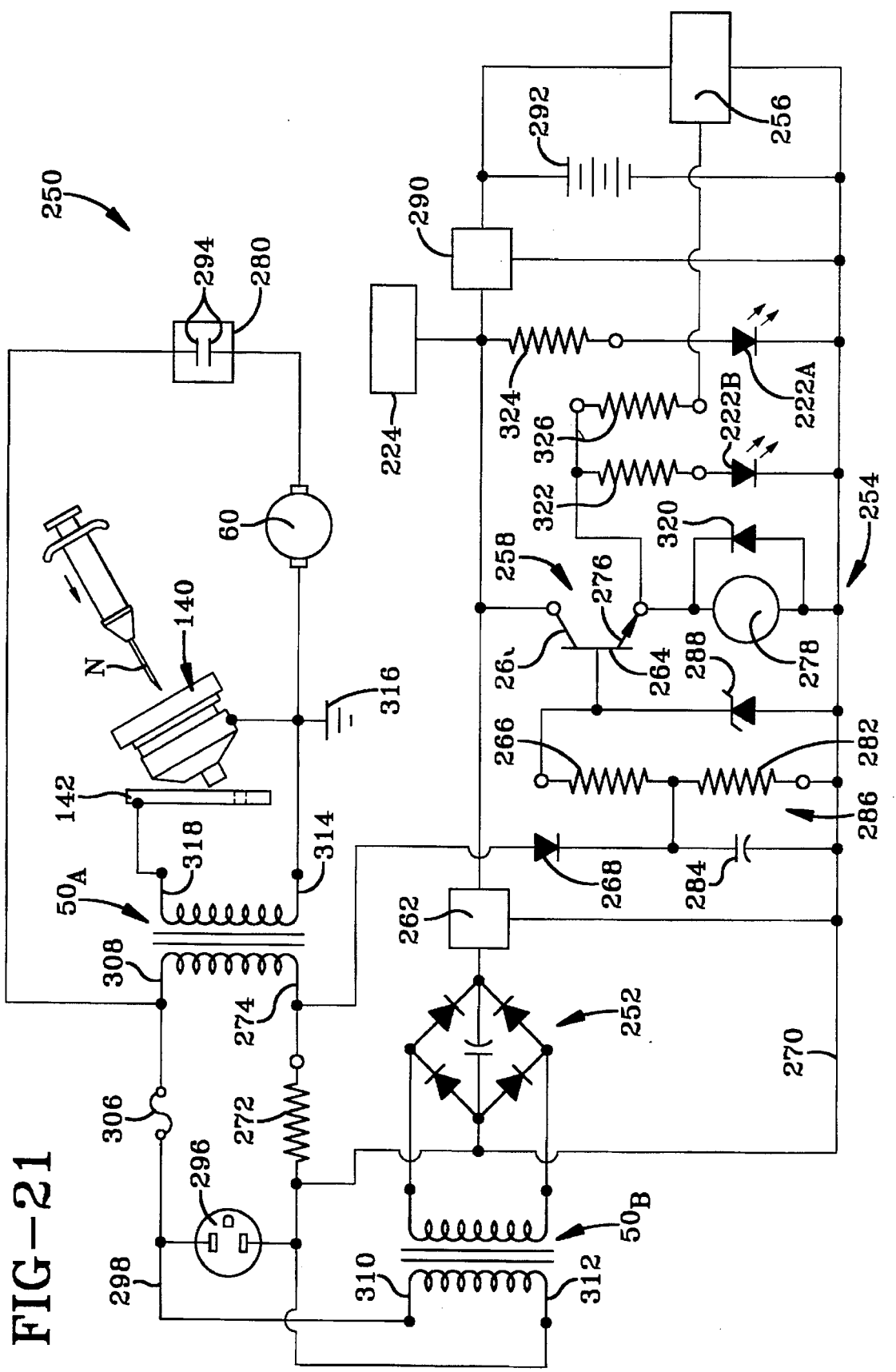

With reference to FIG. 21, representative circuitry 250 for operation from an AC power source is depicted. The circuitry 250 may actually utilize a single, multi-tapped transformer 50, as depicted in the heretofore described structural arrangement of the apparatus 10, but solely for the purpose of clarity the single, multi-tapped transformer 50 will be represented as two transformers $50_A$ and $50_B$. The transformer 50$_A$ will supply the high energy output employed to disintegrate the medical instrument, such as a needle, and the transformer 50$_B$ will supply the required low energy necessary to operate the control circuitry and the desired logic circuits.

Specifically, the transformer 50$_B$ is connected with a conventional, diode bridge rectifier 252 which supplies DC power to a control circuit 254 that furnishes an appropriate count signal to a counter 256. The representative control circuit 254 employs a NPN transistor 258, the collector 260 of which is connected to the rectifier 252 down stream of a voltage regulator 262. The base 264 of the transistor 258 is connected—downstream of a control resistor 266 and a diode 268—to one AC power conductor 270 that feeds the transformer 50$_A$. As shown, the connection to the power conductor 270 may be effected between a shunt resistor 272 and one of the AC power-input taps 274 for the transformer 50$_A$. The emitter 276 of the transistor 258 is connected to send a signal to the counter 256, and power the coil 278 of a control relay switch 280. The base 264 is also connected to one side of a resistor 282 and capacitor 284 connected in parallel as a standard RC timer circuit 286. In fact, that same side of the RC timer circuit 286 is connected between the control resistor 266 and the diode 268. The other side of the RC timer circuit 286 is connected directly to the power conductor 270. A zener diode 288 is also connected between the base 264 and the power conductor 270.

The control circuit 254 also includes a 5.5 volt regulator 290 and may include a rechargeable 5 volt battery 292 which supply the required voltage to the counter 256, even when the apparatus 10 is not plugged into a power source.

The transistor 258 is configured such that when the base 264 is above the cut-off voltage, the transistor 258 is non-conductive. However, when the base voltage is lowered to or below the cut-off voltage—that is, when the base 264 saturates—the transistor 258 will conduct current from the collector 260 to the emitter 276. The current through the transistor 258 will energize the coil 278 of the control relay switch 280 and thereby close the contacts 294 to complete the circuit through the control relay switch 280.

The AC circuitry 250 is connected to an AC power source by a conventional plug 296 that receives line voltage and transmits that voltage to the transformers 50$_A$ and 50$_B$ through the AC power conductors 270 and 298, which may be incorporated in a conventional multi-wire cord 300 (FIG. 4) that passes through an aperture 302 in the rear wall 22 of the primary sub-housing 14. A standard strain reliever 304 may be received within the aperture 302 to transfer mechanical stresses applied to the multi-wire cord 300 exteriorly of the sub-housing 14 from adversely affecting the circuitry within the apparatus 10.

The AC power conductor 298 preferably feeds through a fuse 306 and branches to connect: to one side of the control relay switch 280; to the second power-input tap 308 on transformer 50$_A$; and, to a first, power-input tap 310 on transformer 50$_B$. The other AC power conductor 270 connects to the second, power-input tap 312 on transformer 50$_B$. The electric motor 60 connects to the other side of the control relay switch 280 as well as to the first tap 314 on the secondary side of transformer 50$_A$. At this point it can be observed that the first tap 314 is at ground potential, the ground being represented at 316. The fixedly positioned, first electrode 140 is also connected to the first tap 314 on the secondary side of transformer 50$_A$. The fixed electrode 140 may be insulated by making the protective cap 170 from an insulating material. Even so, having that electrode—which is accessible to the user of the apparatus 10—at ground potential is a definite safety feature. The second, linearly reciprocating electrode 142 is connected to the second tap 318 on the secondary side of transformer 50$_A$.

There are certain other features to the circuitry 250 that should be appreciated. For example, a blocking diode 320 spans the coil 278 of the control relay switch 280 to ensure that only current from the emitter 276 would be able to activate the control relay switch 280. A first pull-up resistor 322 in series with the LED 222B also spans the coil 278 of the control relay switch 280 and provides a visual indication that the coil 278 is receiving power and that the device is operating. LED 222A is provided to show that power is on. The LED 222A can, therefore, be electrically interposed between the output of regulator 262 and AC power supply conductor 270. As depicted, a second pull-up resistor 324 is connected in series between the LED 222A and the output of the regulator 262. The third LED 222C is connected to the counter 256 in a manner similar to the connection of the first two LEDs, and it may be wired in a well known manner to provide a visual indication that the counter has reached a predetermined numerical value. The counter 256 may, of course, be connected to a digital read-out 224 that is depicted in the slanted front surface 220 of the cover 218 for the primary sub-housing 14 to allow the user of the apparatus 10 to know, at least generally, how many medical instruments have been destroyed since the receptacle 16 was last replaced. As depicted in FIG. 21, a current limiting resistor 326 may be included in the signal feed line between the emitter 276 of the transistor 258 and the counter 256.

In order to operate the apparatus 10 a needle N is inserted axially through the fixedly positioned first electrode 140 until it comes into contact with the second electrode 142. The metallic needle thus closes an electrical circuit across the two electrodes 140 and 142 which creates an immediate current flow through the secondary winding of transformer 50$_A$. This current flow is reflected through the shunt resistor 272 which triggers an electrical flow through the zener diode 288 and simultaneously charges the RC timer circuit 286. With the zener diode triggered, the base 264 of the transistor 258 saturates, permitting current to flow through the transistor 258. The current flowing through the transistor 258 is reflected in the coil 278 of the control relay switch 280, closing the contacts 294 of the relay switch 280 to start the motor 60 which rotates the fan member 86 and linearly reciprocates the second electrode 142. The current flow through the needle N, and the engagement of the needle against the movable second electrode 142 electrically destroys the needle to the degree that only the metallic swarf remains.

The RC circuit 286 is designed to force the motor 60 to continue to run for a predetermined period of time after the needle has been destroyed. Specifically, the RC timer circuit is designed so that the fan member 86 will continue to rotate for a preselected period of time. As a general rule, that time is selected to permit the fan member 86 to evacuate a volume of air equal to at least two times the volume of the cartridge 16, thereby precluding a reverse flow of potentially toxic air outwardly through the fixed, first electrode 140.

While only a preferred structural embodiment of my present invention, which is operated by virtue of an AC power source, is disclosed, it is to be clearly understood that the same is susceptible to numerous changes apparent to one skilled in the art. Therefore, the scope of the present invention is not to be limited to the details shown and described but is intended to include all changes and modifications which come within the scope of the appended claims.

As should now be apparent, the present invention teaches a novel and unique apparatus for the electrical destruction of medical instruments in the nature of hypodermic needles and otherwise accomplishes the objects of the invention.

We claim:

1. An apparatus for the electrical destruction of medical instruments comprising:
   a primary sub-housing;
   a cartridge sub-housing demountably secured to said primary sub-housing;
   first and second electrodes disposed within said cartridge sub-housing;
   guide means incorporated in said first electrode for accepting a medical instrument for destruction;
   said first electrode being fixedly positioned with respect to said cartridge sub-housing;
   said guide means directing said medical instrument such that insertion thereof in said guide means effects an electrical connection between said first and second electrodes;
   means for translationally reciprocating said second electrode between fixed limits; and,
   means for energizing said first and second electrodes with a sufficient level of electrical energy to cause the electrical destruction of a medical instrument positioned in electrical contact with said first and second electrodes.

2. An apparatus for the electrical destruction of medical instruments, as set forth in claim 1, wherein:
   said second electrode is mounted for linear reciprocation in said cartridge sub-housing.

3. An apparatus for the electrical destruction of medical instruments, as set forth in claim 2; wherein:
   said first electrode has a central passage extending axially therethrough to receive a medical instrument and to serve as a guide; and,
   said axial passage being disposed at an acute angle with respect to said translationally reciprocating second electrode.

4. An apparatus for the electrical destruction of medical instruments, as set forth in claim 3, wherein:
   said primary sub-housing communicates with the surrounding atmosphere through said axial passage;
   a fan-receiving chamber in said primary sub-housing;
   said fan-receiving chamber communicating with said cartridge sub-housing through a first filter;
   a fan member in said fan-receiving chamber;
   means selectively to operate said fan member when a medical instrument effects an electrical connection across said first and second electrodes; and,
   means to exhaust said fan-receiving chamber to atmosphere through a second filter.

5. An apparatus for the electrical destruction of medical instruments, as set forth in claim 4, wherein:
   said means selectively to operate said fan member when a medical instrument effects an electrical connection across said first and second electrodes also linearly translates said second electrode.

6. An apparatus for the electrical destruction of medical instruments, as set forth in claim 5, wherein:
   a motor disposed in said primary sub-housing operates said fan member and said means to translates said second electrode linearly.

7. An apparatus for the electrical destruction of medical instruments, as set forth in claim 1, wherein:
   a fast-make electrical contact connection is provided between each of said first and second electrodes in said cartridge sub-housing and said primary sub-housing to facilitate removal of said cartridge sub-housing from said primary sub-housing.

8. An apparatus for the electrical destruction of medical instruments comprising:
   a primary sub-housing;
   a cartridge sub-housing demountably secured to said primary sub-housing;
   first and second electrodes disposed within said cartridge sub-housing;
   electrical control circuitry including a low power circuit and a high power circuit;
   an electrical connection selectively effected across said first and second electrodes by a metallic medical instrument to activate said low power circuit;
   first switch means in said low power circuit to activate said high power circuit;
   said high power circuit energizing said first and second electrodes with a sufficient level of electrical energy to cause the electrical destruction of the medical instrument effecting the electrical connection across said first and second electrodes; and,
   means for confining said second electrode to reciprocate linearly with respect to said first electrode.

9. An apparatus for the electrical destruction of medical instruments, as set forth in claim 8, further comprising:
   a second switch means in said high power circuit responsive to closure of said first switch means for activating said high power circuit to conduct destructive electrical current through said medical instrument.

10. An apparatus for the electrical destruction of medical instruments, as set forth in claim 9, further comprising:
    an electrical timer means to extend the operation of said high power circuit for a predetermined period of time after the medical instrument ceases to effect an electrical connection between said first and second electrodes.

11. An apparatus for the electrical destruction of medical instruments comprising:
    a primary sub-housing;
    a cartridge sub-housing demountably secured to said primary sub-housing;
    first red second electrodes disposed within said cartridge sub-housing;
    said first electrode is fixedly supported by said cartridge sub-housing;
    guide means incorporating said first electrode for accepting a medical instrument for destruction;
    said guide means directing said medical instrument such that insertion thereof in said guide means effects an electrical connection between said first and second electrodes;
    means for linearly reciprocating said second electrode between fixed limits;
    said means for linearly reciprocating said second electrode incorporating a cam and follower mechanism;
    said follower mechanism being operatively connected to said second electrode; and,
    means for energizing said first and second electrodes with a sufficient level of electrical energy to cause the electrical destruction of a medical instrument positioned in electrical contact with said first and second electrodes.

12. An apparatus for the electrical destruction of medical instruments comprising:

a primary sub-housing;

a cartridge sub-housing demountably secured to said primary sub-housing;

first and second electrodes disposed within said cartridge sub-housing;

said first electrode is fixedly supported by said cartridge sub-housing;

guide means incorporating said first electrode for accepting a medical instrument for destruction;

said guide means directing said medical instrument such that insertion thereof in said guide means effects an electrical connection between said first and second electrodes;

means for linearly reciprocating said second electrode between fixed limits;

said means for linearly reciprocating said second electrode incorporating an electrode drive shaft rotatably mounted in said primary sub-housing;

a dog presented from said electric drive shaft;

a transfer shaft having opposite ends and rotatably mounted in said cartridge sub-housing;

one end of said transfer shaft having means to engage said dog;

the other end of said transfer shaft having an eccentric drive pin to serve as a cam;

said second electrode mounted for linear reciprocation and having a slot serving as a cam follower and engaged by said eccentric drive pin to reciprocate said second electrode linearly in response to rotation of said electrode drive shaft; and, means for energizing said first and second electrodes with a sufficient level of electrical energy to cause the electrical destruction of a medical instrument positioned in electrical contact with said first and second electrodes.

13. An apparatus for the electrical destruction of medical instruments, as set forth in claim 12, further comprising:

spaced supporting walls interiorly of said cartridge sub-housing;

a guide plate mounted in opposition to said spaced supporting walls;

a slideway recessed in said guide plate;

said slideway also disposed in opposition to said supporting walls; and, said second electrode slidably received in said slideway.

14. An apparatus for the electrical destruction of medical instruments comprising:

a primary sub-housing;

a cartridge sub-housing demountably secured to said primary sub-housing;

first and second electrodes disposed within said cartridge sub-housing;

said first electrode is fixedly supported by said cartridge sub-housing;

guide means incorporating said first electrode for accepting a medical instrument for destruction;

said guide means directing said medical instrument such that insertion thereof in said guide means effects an electrical connection between said first and second electrodes;

means for moving one of said electrodes between fixed limits; and, means for energizing said first and second electrodes with a sufficient level of electrical energy to cause the electrical destruction of a medical instrument positioned in electrical contact with said first and second electrodes a swarf-collecting tray disposed below said first and second electrodes in said cartridge sub-housing; and, a sponge means received in said tray.

* * * * *